United States Patent [19]
Hazbun

[11] Patent Number: 4,791,079
[45] Date of Patent: Dec. 13, 1988

[54] CERAMIC MEMBRANE FOR HYDROCARBON CONVERSION

[75] Inventor: Edward A. Hazbun, Media, Pa.

[73] Assignee: Arco Chemical Company, Newtown Square, Pa.

[21] Appl. No.: 871,746

[22] Filed: Jun. 9, 1986

[51] Int. Cl.$^4$ .................. B01J 21/10; B01J 23/34; B01J 35/00
[52] U.S. Cl. .................. 502/4; 502/324; 502/340
[58] Field of Search .............. 502/4, 340, 527, 324

[56] References Cited

U.S. PATENT DOCUMENTS

| | | |
|---|---|---|
| 3,362,783 | 1/1968 | Leak .................. 502/527 X |
| 3,873,469 | 3/1975 | Foster et al. .................. 502/527 X |
| 3,894,965 | 7/1975 | Foster et al. .................. 502/527 X |
| 3,926,702 | 12/1975 | Oki et al. .................. 502/527 X |
| 3,951,860 | 4/1976 | Acres et al. .................. 502/527 X |
| 4,426,319 | 1/1984 | Blanchard et al. .................. 502/261 X |
| 4,650,781 | 3/1987 | Jones et al. .................. 502/241 |

Primary Examiner—W. J. Shine
Attorney, Agent, or Firm—Craig E. Larson

[57] ABSTRACT

The invention relates to a novel mixed ion and electron conducting catalytic ceramic membrane and to its use in hydrocarbon oxidation and or dehydrogenation processes, the membrane consists of two layers, layer 1 which is an impervious mixed ion and electron conducting ceramic layer and layer 2 which is a porous catalyst-containing ion conducting ceramic layer.

9 Claims, 6 Drawing Sheets

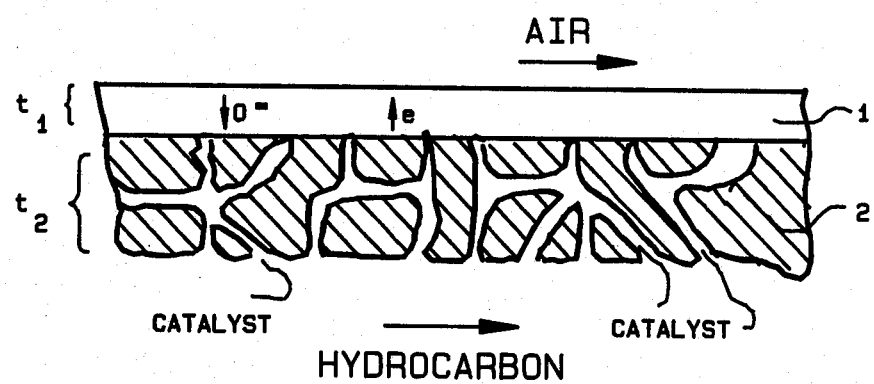
FIGURE-1
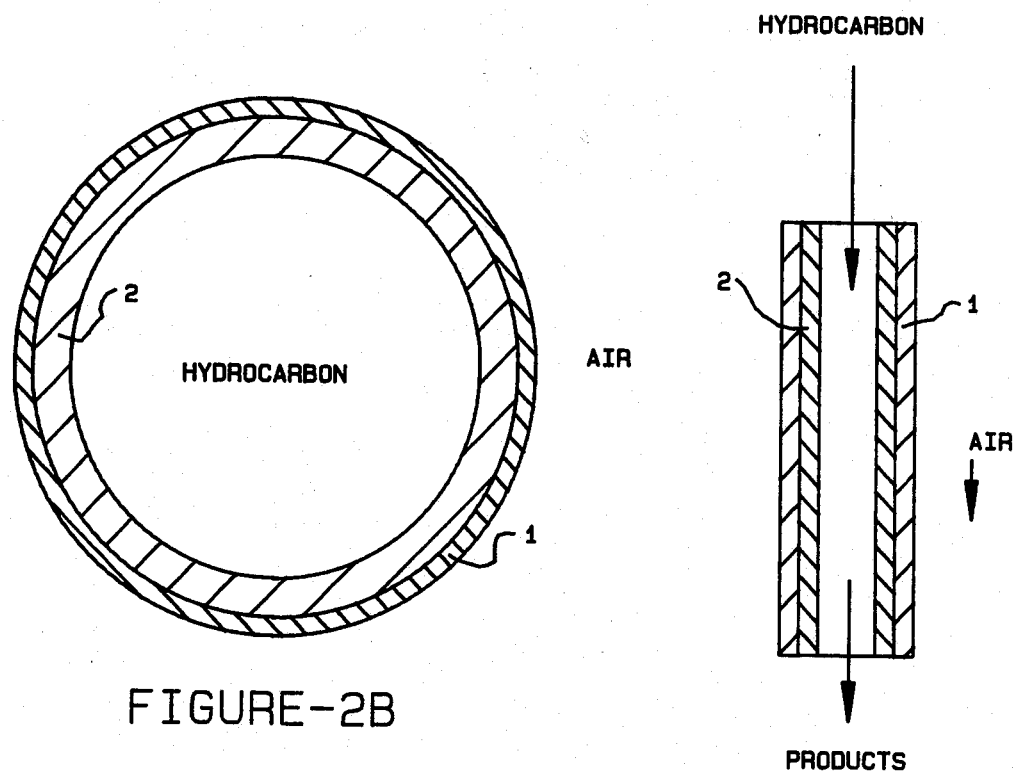
FIGURE-2B
FIGURE-2A

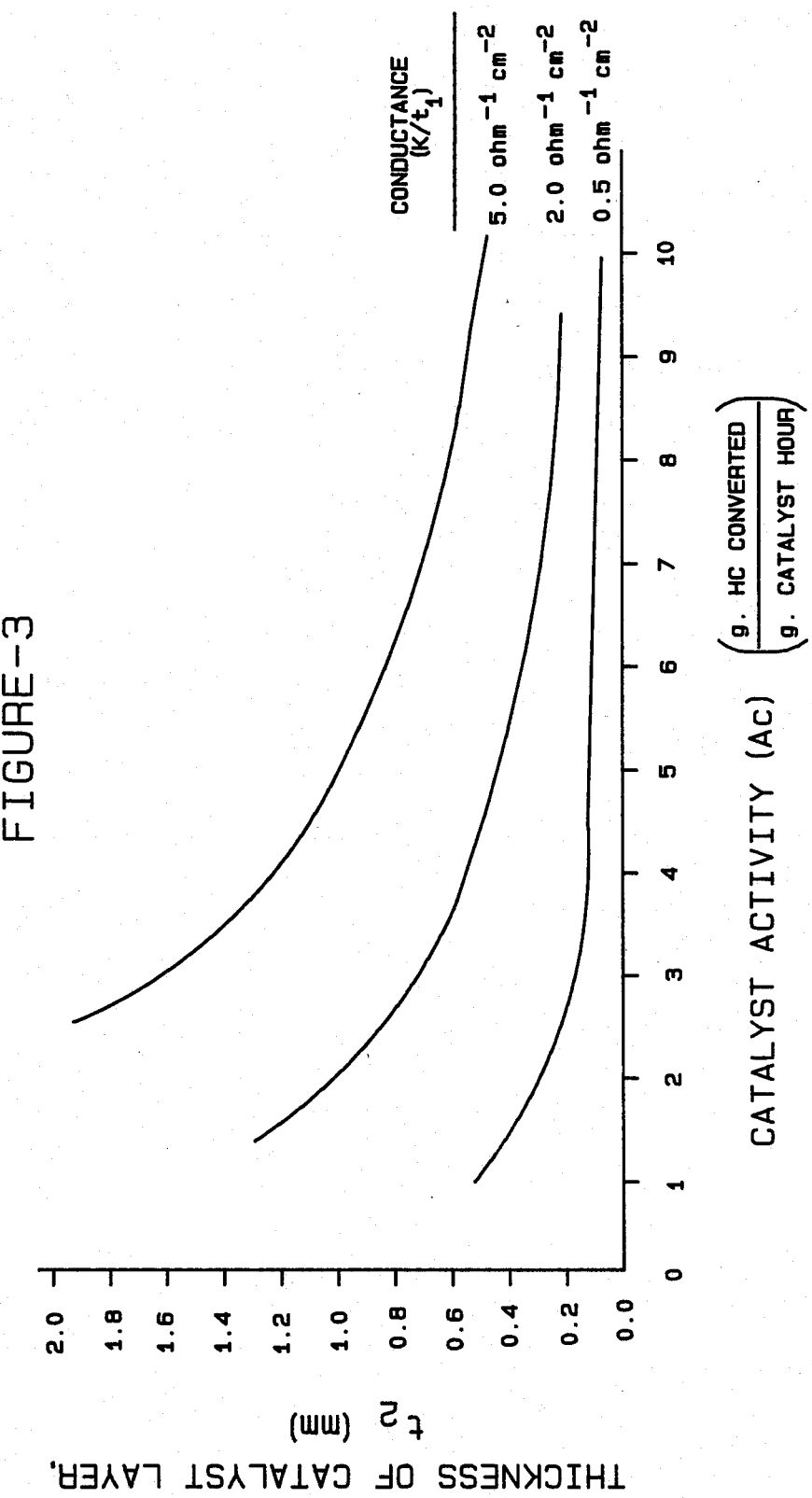

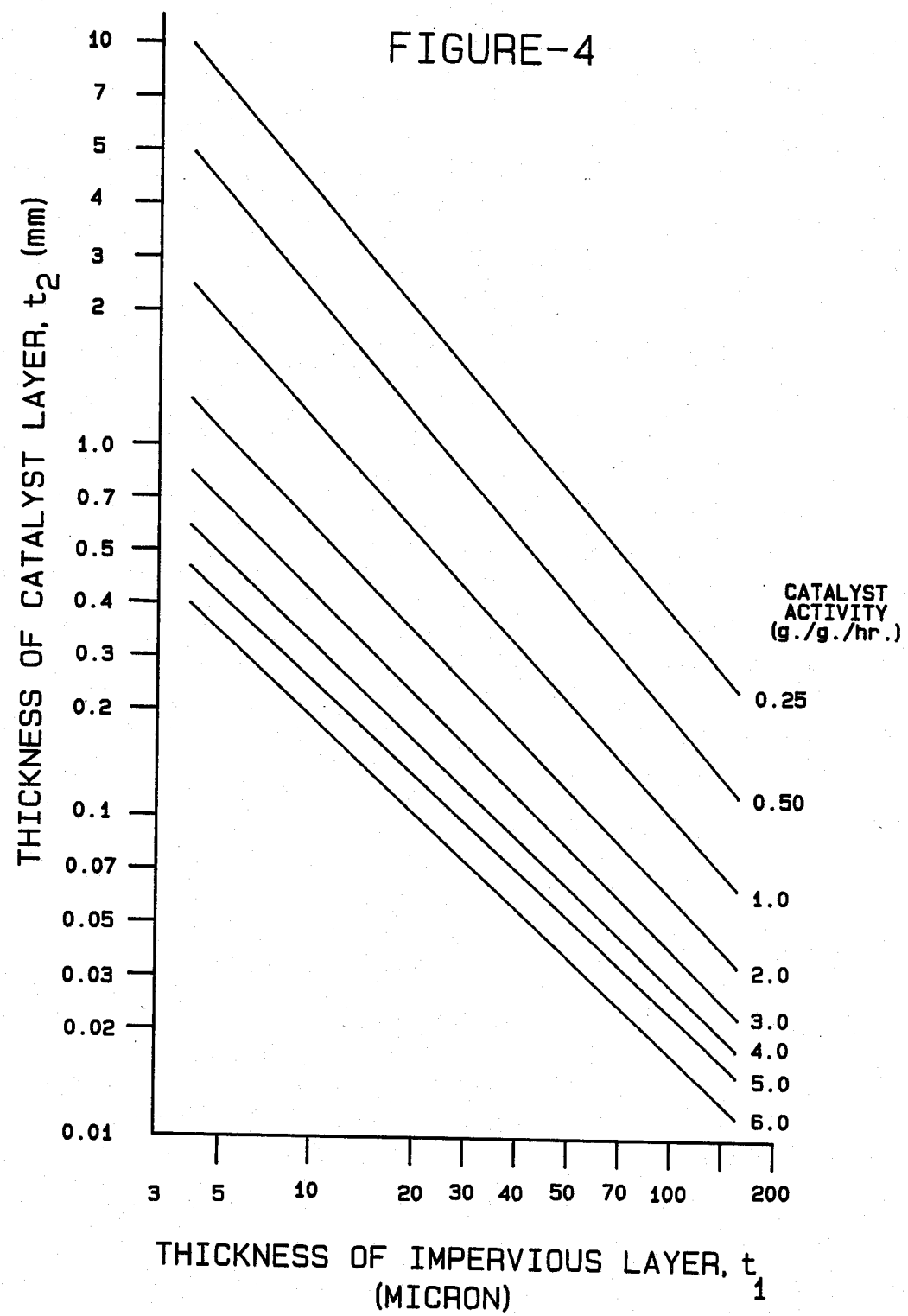

CERAMIC MEMBRANE FOR HYDROCARBON CONVERSION

1. Field of the Invention

The subject invention relates to novel conducting catalytic ceramic membranes and to the use of these novel membranes in various chemical processes such as hydrocarbon oxidations. Catalytic chemical processes are, of course, of critical importance and are widely practiced in a number of technological fields. Frequently, the processes and catalytic systems employed have significant disadvantages in that the reagents required are costly, the apparatus and reaction conditions are somewhat inefficient, and the efficiency of the catalytic conversions fall far short of theoretical. For example, in many oxidation technologies employing oxygen as oxidant, the separation of oxygen from air by low temperature distillation procedures is necessary to produce a reagent oxygen stream. Frequently, the effective catalyst material in such systems is deposited onto or within support particles and these particles placed in a reaction vessel where the reagent gases must be mixed and contacted with the catalyst. Problems in mixing, problems in heat input or removal, depending on the nature of the reaction, and the like are usually encountered in such systems.

2. Description of the Prior Art

A substantial amount of work has been done in the field of the development of ceramic membranes which are ionic conductors. See, for example, "Solid Ionic Conductors" by Shriver et al, *Chemical & Engineering News*, Vol. 63, pp. 43–59 (1985).

An interesting development in the solid ionic conductor field relates to work done in connection with stabilized zirconia materials, especially zirconia doped with oxides of yttrium, scandium, calcium, or magnesium. Such materials are, by now, well known solid electrolytes in which conduction is due essentially to transport of oxygen ions in a lattice with anion vacancies due to presence of the doping material. These ion conductors have found substantial applications, for example, in high temperature fuel cells, oxygen sensors, and the like.

Stabilized zirconia ionic conductors have been used in association with certain catalytic materials in hydrocarbon conversion reactions. For example, Otsuka et al in an article entitled "Catalytic Activity and Selectivity Control for Oxidative Coupling of Methane by Oxygen Pumping Through Yttria Stabilized Zirconia" *Chemistry Letters*, pp 319–322 (1985) describe the oxidative coupling of methane using electrochemically pumped oxygen through yttria stabilized zirconia having silver coated on one surface and silver-bismuth oxide coated on the other surface. In each case, the silver acted as an electrode which was necessary to complete the circuit external of the membrane and thus to permit the desired reaction to proceed. Otsuka et al teach that the oxidative coupling of methane took place only when the circuit was closed by connection of lead wires from both electrodes.

Michaels et al in "Kinetics of Vapor - Phase Electrochemical Oxidative Dehydrogenation of Ethylbenzene," *Journal of Catalysis*, 85, pp. 477–487 (1984) describe electrochemical oxidative dehydrogenation of ethylbenzene to styrene using an yttria stabilized zirconia ionic conductor in the form of a tube with porous platinum electrodes deposited in both inner and outer surfaces which are connected via an external circuit.

Stoukidis et al in, "The Effect of Electrochemical Oxygen Pumping on the Rate and Selectivity of Ethylene Oxidation on Polycrystalline Silver," *Journal of Catalysis*, 70, pp. 137–146 (1981) (also U.S. Pat. No. 4,329,208) describe electrochemical oxidation of ethylene using an yttria stabilized zirconia ionic conductor having a porous silver catalyst film on both surfaces which films function as electrodes and are connected via an external circuit.

An important problem in systems such as those described above is the necessary provision of a catalyst layer deposited on the impervious ion conducting material which layer serves both as catalyst and as external electrode. It is difficult to secure such electrodes to surfaces of the ceramic membrane and to maintain the integrity of the electrode membrane bond during sustained use at the severe conditions normally encountered. Without such electrodes connected externally, however, the desired electrochemical reaction did not proceed.

Stabilized zirconia when doped with titanium dioxide or cerium dioxide and/or with at least one oxide of a metal of group V-B or VI-B demonstrates both ion and electron conductivity. Several ceramic compositions with mixed ion-electron conduction properties have been characterized in the literature. The most notable among these are those claimed in German Patent Application No. 3436597.4, October 1984 assigned to Max-Planck Society, Gottingen. These are titania or vanadia doped materials preferably comprised of 77–88 mole % $ZrO_2$, 10–13 mole % $Y_2O_3$ and 1–10 mole % $TiO_2$. Part or all of the yttria can be replaced by calcia (CaO) or magnesia (MgO) and part of the titania can be replaced by vanadia. Illustrative compositions are illustrated by the following:

88 $ZrO_2$.8 $Y_2O_3$.3 CaO.1 $TiO_2$ (or 1 $VO_2$)
79 $ZrO_2$.11 $Y_2O_3$.10 $TiO_2$

Cerium oxide doped zirconias with mixed conduction properties were also characterized by B. Cales and J. F. Baumard (J. Electrochem Soc., October, 1984, Vol. 131, No. 10).

The titania doped materials have been claimed for use as electrodes in fuel cells and oxygen sensors. The ceria doped materials have been used for the separation of $O_2$ and hydrogen during the dissociation of water at elevated temperatures. Both materials have not been proposed for use in either catalytic hydrocarbon oxidation or hydrocarbon dehydrogenation processes.

BRIEF SUMMARY OF THE INVENTION

The present invention relates to novel two-layer conducting catalytic ceramic membranes and to the use of these membranes in hydrocarbon conversion processes. In particular, the invention provides a novel two-layer membrane in which one layer is an impervious mixed ion and electronic conducting ceramic such as yttria stabilized zirconis which is doped with sufficient $CeO_2$ or titanium dioxide to impart electron conducting characteristics to the ceramic. A second layer associated with the mixed conducting impervious ceramic is a porous ion conducting layer containing a selective hydrocarbon oxidation catalyst.

In accordance with the invention, an oxygen containing gas is contacted with the mixed ion and electron conducting layer while a reactant such as a hydrocarbon is contacted with the porous catalyst-containing layer, the system being maintained at reaction conditions. Oxygen ions pass through the mixed conducting layer and catalytically react with the hydrocarbon in the porous catalyst containing layer. Product is separated from the porous layer while electrons pass through the mixed conducting-layer to balance the system.

THE DRAWINGS

In the attached drawings

FIG. 1 illustrates, in schematic form, the two-layer membrane of the invention.

FIGS. 2a and 2b illustrate a tubular form of the membrane.

FIG. 3 is a plot representing the relationship between the thickness of the catalyst containing layer 2, the catalyst activity and the conductance of layer 1.

FIG. 4 is a plot of the desirable thicknesses of layer 1 and layer 2 for a range of catalyst activities.

DETAILED DESCRIPTION

Figure 5:
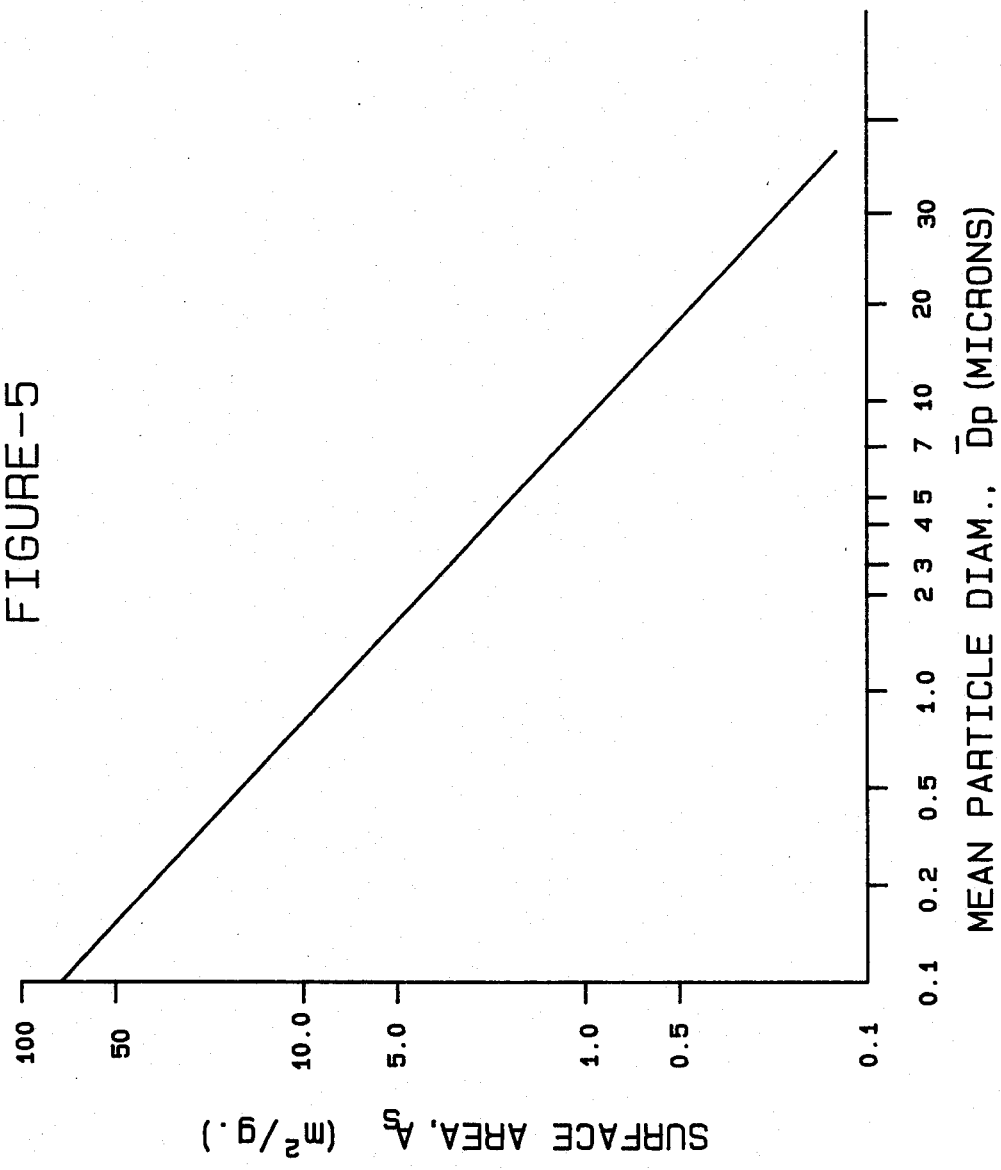
FIG. 5 is a graphical representation of the internal surface area as a function of mean particle diameter for ceramics made by partial sintering of fine stabilized zirconia powders.

Referring to the FIG. 1, layer 1 is an impervious mixed ion and electron conducting ceramic membrane layer having a thickness, $t_1$. Layer 2 is a porous ion conducting catalyst-containing layer having thickness, $t_2$. For purposes of illustration, the pores of layer 2, in which the catalyst may be deposited, have been greatly exaggerated in size.

Suitably, the impervious ion and electron conducting ceramic layer 1 is a stabilized zirconia doped with an oxide which imparts electron conducting characteristics thereto.

Illustratively, layer 1 is comprised of about 77 to 88 mole % zirconia, about 10 to 13 mole % of a stabilizer oxide, and about 1 to 10 mole % of at least one oxide of a Group V-B or VI-B metal or titanium dioxide. The stabilizer oxide is preferably an alkaline earth metal oxide, yttrium or scandium oxide or a rare earth metal oxide; the most preferred are yttrium oxide, calcium oxide and magnesium oxide. Of oxides of Group V-B, VI-B, or titanium dioxide, titanium dioxide is most preferred.

Especially desirable compositions for layer 1 comprise 77 to 88 mole % $ZrO_2$, 11 to 13 mole % $Y_2O_3$, and 1 to 10 mole % $TiO_2$ or alternatively, 1 to 10 mole % $CeO_2$ or $VO_2$. In order to enhance oxygen dissociation, it may be desirable to further provide a thin layer of an oxide of lanthanum chromium, tin, or the like on the surface of layer 1 which contacts the oxygen.

Layer 2 is a porous ion conducting layer having a selective catalyst material incorporated therein. Most preferably, layer 2 is a porous ceramic layer of stabilized zirconia having the catalytic material for the desired hydrocarbon conversion incorporated therein. Preferably the ceramic material is microporous, stabilized zirconia, e.g., zirconia stabilized with yttrium oxide, scandium oxide, calcium oxide or magnesium oxide. The catalyst can be dispersed throughout porous layer 2 or it may be supported on the surface of the layer pores as illustrated in FIG. 1.

In most cases where the catalytic material is itself a metal oxide or a mixture of metal oxides the presence of the catalytic material imparts sufficient electron mobility to layer 2 to balance the electron charges. Where the catalytic material does not provide this mobility, doping material as provided in layer 1, most preferably titanium dioxide, can be incorporated in layer 2. A preferred composition for layer 2 is zirconia stabilized with 8 to 15 mole % calcia, yttria, scandia, magnesia and/or mixtures thereof. For the higher temperature applications, yttria and magnesia are preferred due to their stability to the fluxing effect of alkali metals, such as sodium or potassium, contained in many oxidation catalysts.

Catalytic materials which are known to catalyze various catalytic reactions, especially oxidative conversion reactions, can be used in the novel ceramic membrane of this invention. For example, in the oxidative coupling of methane the catalyst material contains sodium promoted manganese oxide or lithium promoted magnesium oxide. For ethylene oxidation to ethylene oxide, silver oxide is the preferred catalyst. Table 1 provides a general illustration of suitable reactions, operating conditions, composition and thicknesses of membrane layers, as well as suitable catalysts for various embodiments of the invention.

Generally hydrocarbons having from preferably 1 to 8 carbon atoms to about 20 carbon atoms, are reacted in accordance with the invention.

In general, the most appropriate relative thicknesses $t_1$ and $t_2$, of the two membrane layers is determined by consideration of a number of factors. As a broad concept, the rate of oxygen consumption can be estimated for a particular hydrocarbon conversion having in mind the reaction involved, the reaction conditions and the activity of the catalyst system involved. Likewise, the rate of oxygen conduction through the impervious mixed conducting layer 1 can be ascertained for a mixed conductor composition at conditions necessary for the desired reaction. The relative thicknesses, $t_1$ and $t_2$ of the two layers can be determined by equating the rate of oxygen conduction through mixed conducting layer 1 with the rate of oxygen consumption associated with the catalyst containing layer 2.

TABLE 1

| Hydrocarbon | Main Products | Reaction Temp (°C.) | Layer-1 Impervious $ZrO_2.Y_2O_3.TiO_2$ $t_1$ (microns) | Layer 2 Porous & Reactive $ZrO_2.Y_2O_3$ | | Catalyst |
|---|---|---|---|---|---|---|
| | | | | $t_2$ (mm) | A ($m^2/g$) | |
| $CH_4$ | Ethane Ethylene | 700–900 | 30–300 | 1–2 | 5–20 | $MnO_2$.Na or MgO.Li |
| $C_2H_4$ | Ethylene Oxide | 270–350 | 5–40 | 0.2–0.5 | 10–20 | $Ag_2O$ |
| $C_3H_6$ | Propylene Oxide | 300–400 | 7–40 | 0.2–0.5 | 20–50 | Ag/Ca/Ba Oxides or $LaO/SiO_2$ |
| $C_3H_6$ | Acrylonitrile | 400–500 | 10–100 | 0.2–0.5 | 5–20 | Bi/Fe |

TABLE 1-continued

| Hydrocarbon | Main Products | Reaction Temp (°C.) | Layer-1 Impervious $ZrO_2.Y_2O_3.TiO_2$ $t_1$ (microns) | Layer 2 Porous & Reactive $ZrO_2.Y_2O_3$ | | Catalyst |
|---|---|---|---|---|---|---|
| | | | | $t_2$ (mm) | A (m²/g) | |
| & $NH_3$ | | | | | | |
| $C_3H_6$ | Acrolein | 300–400 | 7–50 | 0.2–0.5 | 20–50 | Oxides Mo/Co/W |
| $C_4H_{10}$ | Maleic Anhydride | 350–450 | 10–60 | 0.2–0.7 | 20–40 | Oxides Zn/V/P |
| $iC_4H_8$ | Methacrolein | 300–400 | 7–50 | 0.2–0.8 | 30–50 | Oxides Mo/Co/Fe/Bi |
| $C_2H_6$, $C_3H_8$, $C_4H_{10}$, $C_5H_{12}$ | Olefins and Diolefins | 350–550 | 10–60 | 0.1–1.0 | 20–40 | Oxides W/Sb or Cr/Fe Oxides |

Here $t_1$ is the thickness of Layer 1
$t_2$ is the thickness of Layer 2
A is the surface area of Layer 2

A qualitative relation on a simplified basis can be established for the various systems. For example, at an oxygen consumption of 1.5 gram $O_2$ per gram hydrocarbon feed converted, a simplified relationship can be expressed by the equation $$t_2 = \frac{(0.102)(K)}{(A_c)(t_1)}$$

where K is the oxygen ion conductivity of the impervious mixed conducting layer 1 in $ohm^{-1}.cm^{-1}$, $t_1$ and $t_2$ are expressed in cm., and $A_c$ is the catalyst activity expressed as gram hydrocarbon converted per gram catalyst per hour. This simplified equation neglects the resistivity of the porous layer. It is developed here to derive a qualitative relation between the relative thicknesses of the two layers and to define their dependence on the conductivity of the membrane and the activity of the catalyst in the porous layer. The range of this dependence is depicted in FIG. 2. Low conductance values require the use of thin catalyst layers while low catalyst activity requires the use of a thick catalyst layer. For example, a conductance $(K/t_1)$ of 0.5, which is achievable with a zirconia layer 0.03 mm thick at 850° C., requires a catalyst activity of 5 g/g/hr to provide sufficient reaction sites so that the thickness of the catalyst containing layer ($t_2$) can be kept below 0.1 mm.

FIG. 3 shows the range of thicknesses the two layers may desirably have as a function of catalyst activity, assuming an oxygen conductivity (K) of 0.001 $ohm^{-1} cm^{-1}$.

The conductivity (K) varies exponentially with temperature. This relationship is shown in Table 2 for yttria-stabilized zirconia.

TABLE 2

| T (°C.) | K |
|---|---|
| 1000 | 0.06 |
| 900 | 0.02 |
| 800 | 0.01 |
| 700 | 0.004 |
| 600 | 0.0016 |
| 500 | 0.0010 |
| 400 | 0.0002 |
| 300 | 0.00003 |

For example, at 400° C., K is 0.0002 $ohm^{-1}cm^{-1}$. At this reduced conductivity, the zirconia layer would have to be about 6 microns to allow sufficient oxygen conduction to supply the required oxygen to sustain reaction in a catalyst layer of reasonable thickness (0.2 to 2.0 mm). The thickness of this layer depends on catalyst activity which varies substantially for different catalyst systems.

Clearly, catalyst activity plays a major role in determining the thickness of the porous layer 1. Because the activity of a catalyst ($A_c$) is often directly related to its surface area per unit weight (m²/g), the surface area of the porous layer 1 is an important parameter in the design of the system.

High internal surface area ceramics are produced by pressing or casting the required shape from fine ceramic powder followed by heating to fuse the particles. Depending on the sintering temperature and time used, the particles can be completely or partially fused together to form a solid mass. For partial fusion (about 10% of original particle surfaces are fused), the internal surface area, $A_s$, of the resultant ceramic may be estimated from the mean particle size, $D_p$, of the starting powder as represented in FIG. 5, for yttria-stabilized zirconia at 80% of theoretical density. To obtain porous ceramics with B.E.T. surface areas larger than 5 m²/g, submicron particles are required. These are commercially produced by the "Sol-Gel" process for particles smaller than 0.2 micron, and by the "Solution Precipitation" process for particles in the 0.2 to 1.0 micron size range. Methods for preparing ceramic wafers, cylinders and honeycombs with thin walls for the range of desirable porosities have been developed by various manufacturers and are well known to those skilled in the art.

The novel membranes of the invention can be made by various means. An especially preferred technique involves first preparing a thin walled structure of the thicker of the two layers which is then coated on one side to form a second thin layer. For example, very fine stabilized zirconia slurry can be slip cast in a cylindrical mold to form a tubular membrane. The mold can be moderately pressed to give a preferred wall thickness of about 0.2 to 2.0 mm, and the casting can then be sintered for 1 to 2 hours at 1100° to 1200° C. to give a hard microporous ceramic tube. Either the inside or outside surface can then be coated with a 0.5 to 100 micron thickness of impervious mixed conducting ceramic $ZrO_2.Y_2O_3.TiO_2$ or $ZrO_2.Y_2O_3.CeO_2$ using plasma spraying, flame sputtering or chemical vapor deposition. The desired catalyst component is then deposited within the microporous tube walls by solution precipitation and fixed at the required temperature to activate the catalyst. Alternatively, the catalyst may be incorporated in the microporous layer by mixing the appropriate ingredients in the slurry prior to slip casting or extrusion.

A tubular reactive membrane is alternatively made by pressure or slip-casting the tube using $ZrO_2.Y_2O_3.TiO_2$ ceramic powder which is fired at 1200°–1500° C. to give an impervious tube wall 0.1 to 0.5 mm thick. The porous layer of stabilized zirconia is then applied in the form of a wash coat deposited on the inner or outer surface of the tube using a slurry of monodisperse fine ceramic powder. The wash coat is sintered for 1 to 2 hours at 1100°–1200° C. (preferably 1160° C.) to give a hard microporous layer 0.01 to 0.2 mm thick. The desired catalyst is then deposited within this layer by solution precipitation or evaporation. Alternatively, the catalyst may be incorporated in the wash coat slurry prior to depositing on the ceramic surface.

Similar production methods can be used to fabricate the reactive membrane in thin wafers, films or cellular monolithic structures. The latter have the advantage of providing a large reactive membrane area per unit volume of reactor space. Cellular ceramic structures also provide a high degree of mechanical integrity. They can be fabricated by pressure extrusion methods or by film casting. With film casting, the flat films are corrugated then overlayed to form a cellular structure which is then hardened and fused by firing at 800° to 1500° C.

A relatively simple reactor configuration which can readily be fabricated is a tubular structure illustrated in FIGS. 2a and 2b. FIG. 2b is a cross section of the tube of FIG. 2a showing an outer impervious mixed conducting layer 1 and an inner porous, catalyst containing layer 2. FIG. 2a shows the tubular reaction apparatus wherein hydrocarbon is injected inside the two-membrane tube into contact with the porous, catalyst containing layer 2. The outside impervious mixed conducting layer 1 is in contact with air as depicted. Oxygen from the air passes through the mixed conducting layer 1 and catalytically reacts with the hydrocarbon. Products of the reaction are removed as illustrated.

Figure 6:
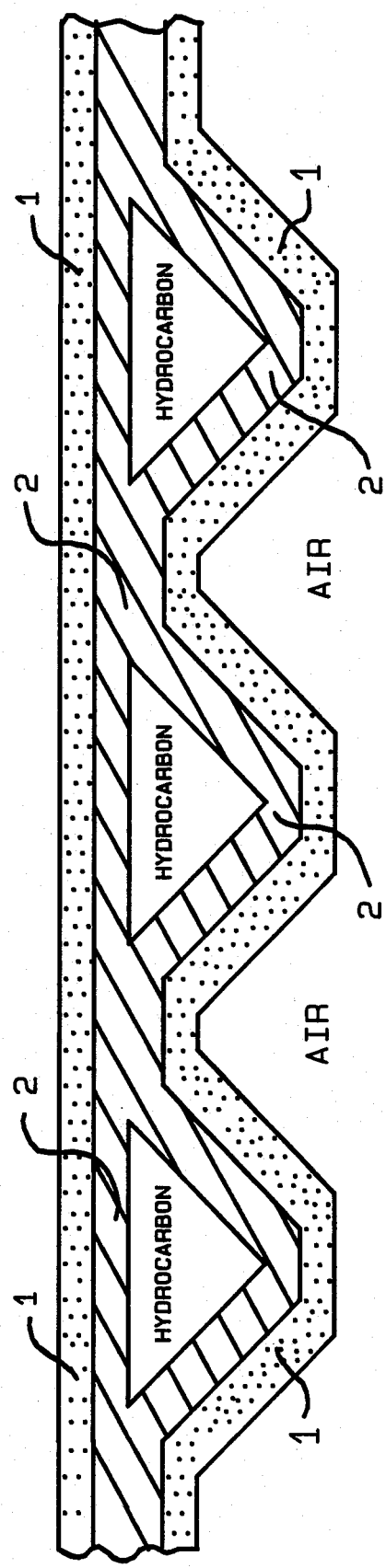
FIGS. 6 and 7 are schematic representations of cellular configurations of the membrane of this invention.
Figure 7:
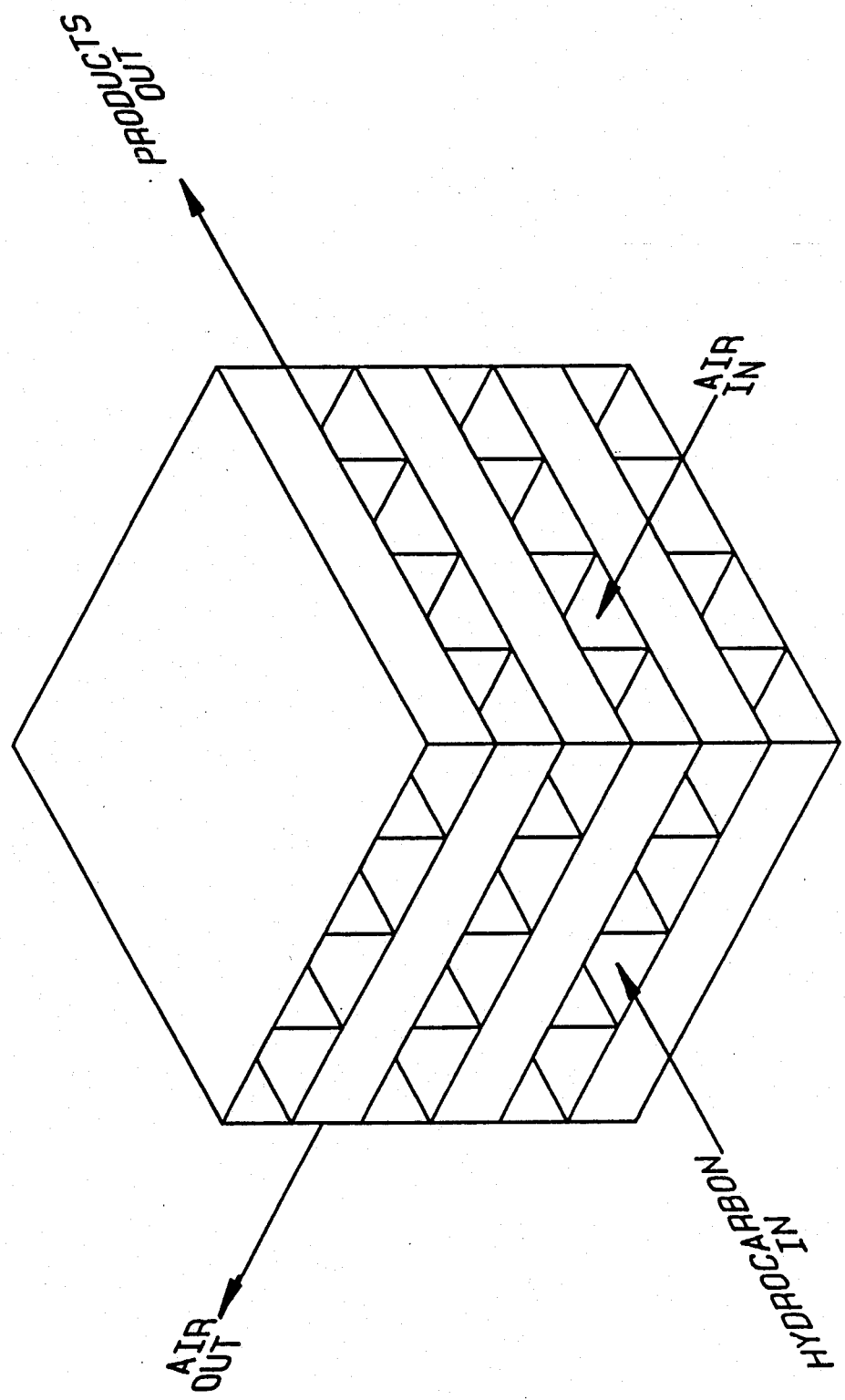

An alternative reactor configuration which is even more preferred are cellular structures such as those illustrated in FIGS. 6 and 7. FIG. 6 illustrates in cross section the multi-cell structure showing the outer impervious mixed conducting layer 1 in contact with air and the inner porous, catalyst containing layer 2 in contact with hydrocarbon. The air and hydrocarbon pass in concurrent or countercurrent flow through adjacent channels.

FIG. 7 represents an alternative configuration wherein the air and hydrocarbon pass through alternative layers at right angles. In this configuration the two layer conducting membrane comprises the horizontal separating structure between alternate hydrocarbon and air zones, the impervious, mixed conducting layer contacting the air zone and the porous, catalyst containing layer contacting the hydrocarbon zone. In this embodiment, the corrugated members in each zone are for purposes of support and distribution.

EXAMPLES

The following examples are offered for purposes of illustration and further explanation of the invention.

EXAMPLE 1

Preparation of Two Layered Tubular Membrane

A preferred configuration of the oxygen conducting membrane is prepared by coating a standard calcia-yttria- or magnesia-stabilized zirconia (CSZ, YSZ or MSZ) tube with a thin uniform coating of mixed conducting zirconia. The selective oxidation catalyst is then deposited by chemical or physical means in the pores of the support tube.

The starting layer of the conductive membrane consists of a porous calcia-stabilized zirconia (CSZ) tube 10 mm I.D. and 1.0 to 2.0 mm thick made by the extrusion of "green" zirconia-calcia paste followed by sintering at elevated temperatures. This standard size SCZ tube is available from several zirconia manufacturers such as Applied Ceramics, Inc. and the Zircoa Division of Corning. It can be fabricated with different porosities ranging from 10 to 50%. Porosities of 20 to 40% are preferred for this application. An impervious layer of yttria-stabilized zirconia doped with titania, 12 mole % yttira, 87 mole % zirconia and 1 mole % titania, about 20 microns thick is then deposited on the outside surface of the tube. This is achieved by electrochemical vapor deposition in which zirconium, yttrium and titanium chlorides are reacted with oxygen on the heated surface of the CSZ tube as generally set forth in U.S. Pat. No. 3,916,041 to Westinghouse Electric Corporation. A mixture of zirconium chloride, yttrim chloride and titanium chloride vapors is prepared in a molar ratio of metal halides selected to give the desired balance between ionic and electronic conductivity. To maximize and equally balance oxygen ions (O=) and electron flow a molar ratio of 87:12:1 (Zr:Y:Ti) is selected. If increased electron flow is desired, then the molar ratio of titanium chloride could be increased. Conversely, if higher O= ions flow is required, then the titanium chloride concentration is decreased. The selected gas mixture is injected into a stream of inert carrier gas, such as argon or helium, to slowly carry the metal chlorides vapors into a reaction chamber over the outside surface of the heated porous tube. A stream of oxygen gas mixed with excess hydrogen is simultaneously passed on the inner side of the tube. A mixed conductor film of 87.0 $ZrO_2$-12.0 $Y_2O_3$-1.0 $TiO_2$ is formed on the outer surface of the tube by the reaction of the metal chlorides with the oxygen permeating through the pores of the tube in accordance with the general reaction:

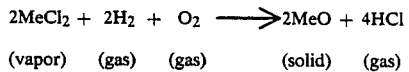

$$2MeCl_2 + 2H_2 + O_2 \longrightarrow 2MeO + 4HCl$$
(vapor)   (gas)   (gas)         (solid)   (gas)

After pore closure, the film thickness is uniformly built up to 20 microns by electrochemical vapor deposition upon controlled exposure in the reaction chamber at 1100° to 1300° C. This method uniquely ensures the fabrication of a tubular, 2-layered membrane with an impervious outer layer of mixed ion- and electron-conducting yttria-stabilized zirconia. The thickness of this layer can be uniformly controlled to a desired thickness ranging from about 2 microns to 60 microns.

The appropriate oxidation catalyst is then deposited within the inner porous layer by impregnation of said layer with an aqueous or organic solution of the catalyst mixture, drying and calcining to fix the catalyst within the passageways of the porous layer. The catalyst components employed depend on the hydrocarbon to be reacted and the products desired from the reaction as illustrated in Examples 2 to 4.

EXAMPLE 2

Ethylene or Propylene Oxidation to Ethylene Oxide or Propylene Oxide

A solution of 6.8 wt % silver nitrate and 10.7 wt % acrylonitrile monomer in hexane with 0.1% azobisisobutyronitrile as initiator is impregnated into the inner porous layer of the ceramic tube and excess solution removed. The tube is then placed in an oven blanketed with an inert gas and maintained at 65° to 70° C. for 1.5 hours. The inner wall of the tube turns mustard yellow indicating the formation of an acrylonitrile/silver nitrate polymer. The tube is then heated under a nitrogen atmosphere as follows: 2 hours at 200° C., 1 hour at 250° C., 1 hour at 300° C. and 2 hours at 400° C. The polymer complex is thus pyrolyzed turning to a grey color and leaving an even deposit of fine metallic silver with a large surface area within the porous layer. When applying a silver catalyst within the porous layer for ethylene or propylene epoxidation, the silver deposited should be from about 0.5 to about 15% by weight of the inner ceramic layer of the tube. If necessary, this may be achieved by repeated applications. Other known methods for applying the silver catalyst may also be employed. These include the use of a variety of silver salts of carboxylic acids with organic amine solubilizing reagents and small amounts of K-salt or Cs-salt or Rb-salt as promoters.

The prepared reactive tubular membrane is tested for catalytic activity by placing the tube in a test apparatus which allows heated air to flow on the outside of the tube and the hydrocarbon gas within the tube. In a representative test, the tube is 15 cm long, 1 cm inner diameter, 2 mm thick containing 8.0 wt % of silver catalyst in the porous layer with an impervious mixed conducting layer of 2 to 10 microns thick.

Direct partial oxidation of ethylene-to-ethylene oxide is conducted as follows: The reactive tube is heated to 250°-400° C. by passing a preheated air stream on the outside surface and preheated nitrogen stream on the inner surface for 2 hours. Once the wall temperature reaches the desired temperature, the nitrogen stream is gradually replaced with pure ethylene gas. The inner wall temperature is monitored and the air stream temperature is adjusted to control the inner wall temperature at a suitable temperature between 250°-400° C. The gas pressure on both sides of the tube is maintained between 15 and 30 psig. The ethylene flow rate is adjusted so that about 10% of the ethylene is converted at a selectivity to ethylene oxide in excess of 75%. The air stream flow rate is adjusted to maintain good heat transfer and uniform tube wall temperature.

Direct partial oxidation of propylene to propylene oxide is conducted in the same manner at ethylene oxide. The reaction temperature is however maintained between 300° to 500° C. and the propylene flow within the tube is adjusted so that about 10 to 15% of the propylene is converted at a selectivity to propylene oxide in excess of 30%. Higher propylene conversion may be achieved by diluting the propylene feed with methane, ethane or propane and operating the reactor at higher temperatures. Higher selectivity to propylene oxide may be attained by adding calcium and barium components to the silver catalyst. alternatively, lanthanum oxide catalyst may be deposited in the porous layer to catalyze the propylene oxide reaction.

EXAMPLE 3

Oxidative Dehydrogenation of Mono-Olefins

Equal molar amounts of ammonium salts of tungstenic acid ($WO_3.H_2O$) and antimonic acid ($Sb_2O_3.H_2O$) are dissolved in water so that a W/Sb molar ratio of 1.0 is achieved. The resultant saturated solution is circulated through the tubular ceramic membrane until the inner porous wall is saturated with the salt solution. The tube is drained then dried by heating to 150° C. in an oven for two hours. It is then calcined at 500° to 600° C. for two hours to fix the $WO_3.Sb_2O_3$ catalyst within the pores of the inner porous ceramic layer. The tube is then mounted in the test apparatus and preheated to 400°-600° C. by passing a heated air stream on the outside of the tube and heated nitrogen inside the tube. The nitrogen stream is then gradually replaced with the mono-olefin stream to be reacted. When butene-1 is fed to the test reactor the following results are obtained: at a temperature of 462° C., 30% of the butene-1 fed is converted to butadiene at 92% selectivity; and at a temperature of 505° C., 57% of the butene-1 is converted with a selectivity to butadiene of 88%.

The reactor may be charged with several variations of the similar catalysts adapted for the oxidative dehydrogenation of propane to propylene, butane to n-butene, isobutane to isobutene, pentane to pentenes, isomylenes to isoprene and other alkanes to the corresponding alkenes as well as olefins to the corresponding diolefins.

EXAMPLE 4

Oxidative Coupling of Methane

A tubular membrane consisting of an impervious outer layer of mixed conducting zirconia having a composition 10 yttria, 89 $ZrO_2$, 1 $TiO_2$, about 50 microns thick and a porous inner layer of magnesia stabilized zirconia (87.0 $ZrO_2$-13.0 MgO) 1 to 2 mm thick is fabricated as described above. The inner layer is then activated with a manganese oxide based catalyst as follows: a saturated aqueous solution of sodium permanganate is circulated within the tube to impregnate the porous layer. The solution is drained and the tube is dried by heating at 150° to 200° C. for 2 hours. Dry sodium permanganate is thus deposited within the pores of the $ZrO_2.MgO$ ceramic. It is then heated in steps to 1000° C. and held for 10 to 15 hours at 1000° to 1200° C. to partially diffuse and react the deposited $NaMnO_4$ with the $ZrO_2.MgO$ substrate within the porous layer. The resultant catalyst formed within the pores is of the general formula:

$$MnNa_aMg_bZr_cO_x,$$

wherein a is in the range 0.01 to 10, b is in the range 0.1 to 90, and c in the range of 0.2 to 45. When calcia stabilized zirconia is used for the porous layer, the resultant catalyst composition would be of the general formula:

$$MnNa_aCa_bZr_cO_x$$

Furthermore, other alkali metals such as K and Li may be substituted for the Na. For additional description of such catalysts, reference is made to U.S. patent application Ser. No. 683,119, filed Dec. 18, 1984, now U.S. Pat. No. 4,650,786 the disclosure of which is incorporated herein by reference.

The now reactive tubular membrane is tested for methane conversion activity by placing the tube in a test apparatus which allows heated air or oxygen to flow outside the tube and the methane gas within the tube. In a representative test, the tube is preheated to 900° C. and methane is gradually introduced inside the tube with an inert gas carrier. The air flow around the tube is adjusted to maintain the inner temperature between 800° and 1000° C. The reaction of methane with the oxygen conducted through the mixed conducting membrane takes place at the catalytic Mn sites resulting in higher hydrocarbon products, coproduct water and some $H_2$ and carbon oxides. The degree of methane conversion achieved depends on the temperature, the level of nitrogen dilution and the flow rate. Conversions of 10 to 50% of the methane feed at selectivities in excess of 50% to higher hydrocarbons are achievable at 850° C. methane conversion is 30% and the selectivity to higher hydrocarbon is 60%. The hydrocarbons produced are predominantly ethane, propane, butane with some olefins.

EXAMPLE 5

Synthesis of Ethylene and Ethane from Methane

The tubular ceramic membrane in example 4 is activated by depositing a solution of lithium carbonate in the porous layer and heating to 465° C. in an oxygen atmosphere forming a layer of 3.0 wt % Li/MgO catalyst within the pores of the magnesia stabilized zirconia. Methane is then reacted within the tube by oxygen ion ($O^=$) conduction through the mixed conductor layer at 700° to 750° C. A product yield of 20 to 25% $C_2$ compounds is obtained at 50 to 60% selectivity and 35 to 45% conversion.

EXAMPLE 6

Cellular Membrane

A second configuration of this reactive membrane that is preferred for large sale commercial application is a cellular form of the invention which can be fabricated in various monolithic shapes.

The porous layer of the ceramic membrane consists of a monolithic structure, produced by the extrusion of stabilized zirconia paste followed by firing at elevated temperatures. Several forms of these cellular structures are commercially available in a wide range of cell dimensions, wall thickness and porosity. In addition to stabilized zirconia, they are available in Cordierite ($2MgO.2Al_2O_3.5SiO_2$), Mullite ($3 Al_2O_3.2SiO_2$), Spinel ($MgO.Al_2O_3$) and mixtures thereof. The standard dimensions are available from Corning Glass Company tradenamed CELCOR TM ceramics and from Applied Ceramics Company tradenamed VERSAGRID TM honeycomb ceramics. The impervious layer is applied to one side of the porous walls by electrochemical deposition methods similar to those described in Example 1 above. In this instance the monolithic structure is manifolded on both ends so that the $ZrCl_4$, $YCl_3$ and $TiCl_4$ in the $N_2$ carrier gas stream is passed through alternate cells in the structure. Oxygen, hydrogen or steam is passed through the adjoining cells. An impervious mixed conducting layer is deposited by electrochemical reaction at the pores inlets on the MeCl side of the cellular walls. The desired catalyst may be deposited in the porous layer by the methods described in Examples 2 to 5, the catalyst solutions being circulated on the uncoated side of the cellular wall.

This configuration of the membrane provides a structure of large surface areas within small volumes. It is very beneficial in large scale hydrocarbon oxidation to support the catalysts and to provide a large heat transfer area for heat removal.

I claim:

1. A ceramic membrane structure comprised of a first layer which is a mixed oxygen ion and electron conducting impervious ceramic layer and a second layer which is associated with said first layer and which is a catalyst-containing porous ion conducting ceramic layer.

2. A ceramic membrane structure comprised of first layer which is mixed oxygen ion and electron conducting impervious stabilized zirconia ceramic doped with a Group-VB, VIB or titanium oxide, and a second layer which is associated with said first layer and which is a porous, catalyst-containing, stabilized zirconia ceramic layer.

3. The structure of claim 1 wherein said catalyst-containing layer contains an oxidative conversion catalyst.

4. The structure of claim 3 wherein the catalyst is sodium promoted manganese oxide complex.

5. The structure of claim 3 wherein the catalyst is lithium promoted magnesium oxide complex.

6. The structure of claim 1 wherein said membrane structure is tubular.

7. The structure of claim 1 wherein said membrane structure is a cellular structure.

8. A ceramic membrane structure comprised of a first layer which is a mixed oxygen ion and electron conducting impervious ceramic layer comprised of about 77–88 mole % zirconia, about 10–13 mole % yttria, and about 1–10 mole % titania, and a second layer which is associated with said first layer and which is a catalyst-containing porous ceramic layer.

9. A ceramic membrane structure comprised of a first layer which is a mixed oxygen ion and electron conducting impervious ceramic layer and a second layer which is associated with said first layer and which is a catalyst-containing porous ceramic layer comprised of zirconia stabilized with about 8 to 15 mole % calcia, yttria, scandia, magnesia and/or mixtures thereof.

* * * * *